United States Patent [19]

Parsons et al.

[11] Patent Number: 5,270,166
[45] Date of Patent: Dec. 14, 1993

[54] IMMUNOASSAYS EMPLOYING GENERIC ANTI-HAPTEN ANTIBODIES AND MATERIALS FOR USE THEREIN

[75] Inventors: Robert Parsons, Libertyville; Robert Kowal, Vernon Hills; Vincent T. Yue, Deerfield, all of Ill.

[73] Assignee: Abbott Laboratories, Abbott Park, Ill.

[21] Appl. No.: 859,772

[22] Filed: Mar. 30, 1992

[51] Int. Cl.$^5$ ............................................. G01N 33/546
[52] U.S. Cl. ..................................... 435/7.4; 436/520;
436/525; 436/816; 436/817; 436/822; 436/901;
436/523; 436/533; 436/534; 435/973; 435/807
[58] Field of Search ....................... 435/7.4, 7.92, 7.93,
435/7.94, 973, 975; 436/518, 520, 523, 525, 531,
533, 536, 808, 807, 816, 817, 822, 524, 815, 521;
356/246, 427, 440, 441

[56] References Cited

U.S. PATENT DOCUMENTS 3,654,090  4/1972  Schurrs .......................... 436/518 X
4,678,331  7/1987  Perry ................................. 356/246
4,745,075  5/1988  Haofield et al. ..................... 436/523

FOREIGN PATENT DOCUMENTS 0177191  4/1986  European Pat. Off. .

OTHER PUBLICATIONS

Seradyn, Inc., "Microparticle Immunoassay Techniques", 2nd Edition, (1988), pp. 5-6.

*Primary Examiner*—Esther L. Kepplinger
*Assistant Examiner*—Susan C. Wolski
*Attorney, Agent, or Firm*—Wean Khing Wong

[57] ABSTRACT

The present invention relates to immunoassay methods for detecting and measuring the amount of an analyte in a sample by means of generic anti-hapten antibodies. Also disclosed are multi-analyte immunoassay methods. Reagents, devices, and kits using the anti-hapten antibodies are also disclosed. The present invention also relates to dyed erythrocytes, preferably fixed, which are coated with antibodies. Also disclosed is the use of these dyed erythrocytes in agglutination assays to detect and measure the presence of an analyte in a sample. The analyte can be a hapten, an antigen, or an antibody. Also included are agglutination assays, compositions and kits using these dyed and coated erythrocytes.

16 Claims, 5 Drawing Sheets

IMMUNOASSAYS EMPLOYING GENERIC ANTI-HAPTEN ANTIBODIES AND MATERIALS FOR USE THEREIN

FIELD OF INVENTION

This invention relates to the field of immunoassays.

BACKGROUND OF THE INVENTION

In-vitro diagnostic tests via immunoassays typically involve antibodies with specific binding affinity toward the analytes of interest. In such test configurations, antigenic analytes either bind directly with the antibody or compete with a hapten-label conjugate (competition assay).

In the former case, the antibody-antigen complex may be allowed to grow as in agglutination assays. Alternatively, in sandwich assays, another antibody with affinity to the antigen can be conjugated to a signal label and allowed to bind the primary antibody-antigen complex. The signal response is directly proportional to the analyte concentration.

In competition assays, competition is established between the analytes, typically small molecules in nature, and the hapten-label conjugates. The signal response is inversely proportional to the analyte concentration.

Most target analytes can, in principle, be detected using either the competition assay or the sandwich assay format. While there are numerous examples where the stated methods served the purpose very well, the utility of these approaches however, were somewhat limited in that a single assay is specific for a single analyte only. A multi-analyte assay is difficult.

The following exemplifies the different available immunoassay formats. Mochida et al., U.S. Pat. No. 4,185,084 discloses non-homogeneous assays with wash and separation steps. An insolubilized anti-analyte antibody acts as a primary capture phase for the analyte which is conjugated to a hapten (hapten-analyte conjugate). After washing, soluble labelled anti-hapten antibody is added and the complex of (anti-analyte antibody/hapten-analyte conjugate/anti-hapten antibody) is detected. Sadeh et al, U.S. Pat. No. 4,243,749, discloses another similar sandwich assay format. Sadeh et al., is specifically oriented towards measuring low molecular weight (hapten) antigens. The unknown analyte and the hapten-analyte conjugate are incubated together with the insoluble anti-analyte antibody in a competitive assay format. Following the wash step, soluble labeled anti-hapten antibody is added and the system is washed again and the labeled complex of (anti-analyte antibody/hapten-analyte conjugate/anti-hapten antibody) detected.

Kang et al., *Clin. Chem.*, 32(9):1682–1686 (1986) describes two assay formats. The first assay format presents an enzyme immunoassay which uses an anti-hapten antibody coated microparticle (the common capture particle), an anti-analyte antibody conjugated to a hapten (hapten-anti-analyte-antibody conjugate), and a labeled anti-analyte antibody. If the analyte is present in a sample, a complex of (anti-hapten antibody coated microparticle/hapten-anti-analyte-antibody conjugate/analyte/labeled anti-analyte antibody) is formed and detected. Fluorescein serves as the capture hapten. The microparticle is a latex particle.

Kang et al.'s second assay format is similar to that of Bunting, U.S. Pat. No. 4,271,140. The assay format consists of an anti-hapten antibody bound to a solid phase, a hapten conjugated to an anti-analyte antibody (hapten-anti-analyte antibody) and labeled analyte. The complex of all three components are detected.

In agglutination assays, either the antibodies or the antigens (or hapten) may be bound to small particles. The particles that have been used as agglutinable carriers include latex, charcoal, kaolinite, bentonite, inorganic colloidal particles, as well as both microbial cells and erythrocytes. See Mochida, U.S. Pat. No. 4,308,026. When these coated particles (coated with either antibodies or antigens) are mixed with samples containing antigens or antibodies, the coated particles would form visually detectable agglutination. Agglutination is characterized by the clumping of the latex polymer particles from an otherwise smooth suspension. Qualitative latex agglutination tests can be carried out on a simple slide without the aid of any instrumentation. More than one antigen can be detected simultaneously by means of differently colored latex particles which have each been sensitized with antibodies of different specificity and then mixed together. Hadfield, S. G., et al., *J. Immunol Methods*, 97: 153–8 (1987). Hadfield et al, U.S. Pat. No. 4,745,075 May 17, 1988. U.S. Pat. No. 4,419,453 further discloses latex particles dyed with Amocid yellow, brilliant crocein 3BA red dye, and Calco Oil Blue N Dye. U.S. Pat. No. 4,745,075 discloses that there are also marketed test kits for the grouping of Beta Haemolytic Streptococci which include reagents in which the solid phase is a suspension of killed red-dyed or blue-dyed *Staphylococcus aureus* cells.

Hillyard et al., U.S. Pat. No. 5,086,002, discloses an erythrocyte agglutination assay in which the agglutination reagent comprises at least one erythrocyte binding molecule coupled to at least one specific analyte binding molecule wherein the erythrocyte binding molecule does not cause agglutination when incubated with erythrocytes in the absence of analyte (in the case of a direct assay) or analyte binding reagent (in the case of an indirect assay). The erythrocytes are preferably endogenous to the blood sample to be tested. Mixtures of conjugates and conjugates of analyte analogues with erythrocyte binding molecules may also be used as agglutination reagents. Chang, U.S. Pat. No. 4,433,059, discloses an agglutination immunoassay reagent in which two antibodies are covalently linked "tail-to-tail", so as not to alter their specificity. One antibody is specific for an antigen borne by an indicator substance, such as an erythrocytes.

SUMMARY OF THE INVENTION

One aspect of the invention presents an immunoassay for an analyte, (A). The immunoassay uses an anti-hapten antibody ($\alpha$H), a hapten conjugated to an analyte (H-A), and an anti-analyte antibody ($\alpha$A). The A can be labelled to allow for detection. If the analyte is not present in the sample, a complex of ($\alpha$H)(H-A)($\alpha$A) is formed. If the analyte is present in the sample, the analyte will compete with (H-A) for ($\alpha$A), to form the complex of ($\alpha$A)(A). After an appropriate incubation period, the presence of ($\alpha$H)(H-A)($\alpha$A) or ($\alpha$A)(A) is detected or measured. The amount of ($\alpha$H)(H-)($\alpha$A) is inversely proportional to the amount of analyte in the sample, whereas the amount of ($\alpha$A)(A) is directly proportional to the presence of the analyte in the sample.

The above assay can be presented in an agglutination assay format wherein the anti-hapten antibody is coated onto a particle, preferably a microparticle. In this case, a separation step is not required. The formation of the complex of (αH)(H-A)(αA) can be visually detected in the agglutination of the coated particles.

Another aspect of the invention presents an immunoassay for an antibody (αA) in a sample, by exposing the sample to anti-hapten antibodies (αH), and hapten conjugated to antigen of the antibody to be assayed (H-Ag), and labeled antibody (αA*). The resulting complex of (αH)(H-Ag)(αA*), if any, is inversely proportional to the amount of the antibody (A) in the sample, and the amount of remaining (αA*) is directly proportional to the amount of (αA) in the sample.

Another aspect of the invention presents a direct agglutination assay for antibodies (αA) in a sample, which exposes the sample to particles coated with anti-hapten antibodies (P-αH), and conjugates comprising haptens and antigens to the antibodies (H-Ag). Agglutination of the coated particles is directly proportional to the amount of antibodies in the sample.

Another aspect of the invention presents the preceding agglutination assays with the addition of particles not coated with the anti-hapten antibodies, the color of the coated and uncoated particles are such that they enhance visualization of the agglutination or lack thereof.

Another aspect of the invention presents multi-analyte assays which employ anti-hapten antibodies attached to a solid phase, and the solid phase is preferably a particle. The multi-analyte assays can be conducted in competitive agglutination assay formats.

Another aspect of the invention presents reagents and kits for conducting the above assays.

Another aspect of the invention presents a multi-analyte assay device with different chambers, wherein each chamber contains a reagent for a specific analyte, and the reagent is a hapten conjugated to the specific analyte to be assayed.

Another aspect of the invention presents dyed and preferably fixed erythrocytes which have been coated with anti-hapten antibodies, and can be used in agglutination assays. Also presented are: agglutination assay kits containing the dyed and coated erythrocytes, and compositions comprising dyed and coated erythrocytes for use in agglutination assays.

DETAILED DESCRIPTION OF THE INVENTION

The invention presents an immunoassay for an analyte (A). The immunoassay uses an anti-hapten antibody (αH), a hapten conjugated to an analyte (H-A), and an anti-analyte antibody (αA). The αA can be labelled to allow for detection. If the analyte is not present in the sample, a complex of (αH)(H-A)(αA) is formed. If the analyte is present in the sample, the analyte will compete with (H-A) for (αA), to form the complex of (αA)(A). After an appropriate period of incubation, the complex of (αH)(H-A)(αA) is then separated from the uncomplexed H-A, αA, or the complex of (αA)(A), if any. The presence of (αH)(H-A)(αA) or (αA)(A) is then detected or measured. The amount of (αH)(H-A)(αA) is inversely proportional to the amount of analyte in the sample, whereas the amount of (αA)(A) is directly proportional to the presence of the analyte in the sample.

The above assay can be conducted in a competitive assay format, whereby the anti-hapten antibody can be attached to a solid phase.

The above assay can also be presented in an agglutination assay format wherein the anti-hapten antibody is coated onto a particle, preferably a microparticle. In agglutination assays, no separation steps are required. The formation of the complex of (αH)(H-A)(αA) can be visually detected in the agglutination of the coated particles.

Also disclosed is a direct agglutination assay for the analyte with multiple epitopes using particles coated with anti-hapten antibodies (P-αH), conjugates of hapten and antibodies against the analyte (H-αA), the degree of agglutination of the coated particles is directly proportional with the presence of the analyte in the sample.

Also disclosed herein is an immunoassay method for detecting and measuring an antibody (αA) in a sample, by exposing the sample to anti-hapten antibodies (αH), and hapten conjugated to antigen to which the antibody binds (H-Ag), and labeled antibody (αA*). The resulting complex of (αH)(H-Ag)(αA*), if any, is inversely proportional to the amount of the antibody (αA) in the sample, and the amount of remaining (αA*) is directly proportional to the amount of (αA) in the sample.

Also disclosed herein is a direct agglutination assay for antibodies (αA) in a sample, which exposes the sample to particles coated with anti-hapten antibodies (P-αH), and conjugates comprising haptens and antigens to the antibodies (H-Ag). Agglutination of the coated particles is directly proportional to the amount of antibodies in the sample.

Also disclosed herein are multi-analyte assays and assay devices which employ anti-hapten antibodies. Reagents and kits for conducting all the above assays, for example dyed fixed erythrocytes coated with anti-hapten antibodies, are also disclosed herein.

Assay Formats

The invention can be practised in formats that include: homogenous, sandwich, competitive, and agglutination assay formats. In the sandwich or competitive assay formats, the anti-hapten antibodies can be attached to a solid phase, thus rendering the solid phase into a generic solid phase that can be used to assay different analytes. Materials for solid phase can be any of those used for immunoassays. Natural, synthetic or naturally occurring materials that are synthetically modified can be used. They include: polysaccharides, e.g., cellulose materials including paper, cellulose and cellulose derivatives such as cellulose acetate and nitrocellulose; silica; fiberglass; inorganic materials such as deactivated alumin, diatomaceous earth or other inorganic finely divided material uniformly dispersed in a porous polymer matrix made of polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as sillica gel, agarose, dextran and gelatin; polymeric films such as polyacrylamide; magnetic particles; microtitre plates; polystyrene tubes; protein binding membranes; agarose; Sephadex (Pharmacia Fine Chemicals, Inc., Piscataway, N.J.); Trisacryl (Pointet-Girard, France); sillicon particles; porous fibrous matrixes etc.

One embodiment of the invention presents a competitive assay format wherein the sample for which the analytes are to be assayed is mixed with hapten-analyte conjugate (H-A) and antibodies to the specific analytes to be assayed (anti-analyte antibodies, $\alpha A$). The anti-analyte antibodies are labeled for detection, e.g. with enzyme, radioactive, fluorescent, or chemical labels. The mixture is then passed over the solid phase, to which anti-hapten antibodies have been attached, and incubated for a sufficient time to allow the complex of $(\alpha H)(H-A)(\alpha A)$ to form. Next, the unbound reagents are separated, e.g. the unbound reagents are dissolved in an aqueous medium and washed away from the solid phase and the formation of the complex of $(\alpha H)(H-A)(\alpha A)$ on the solid phase is detected by detecting the labeled $\alpha A$. If the analyte is not present, the complex will be present. If the sample contains the analytes, the analytes will bind the labeled anti-analyte antibodies, and no complex will be present, or the amount of complexes will be reduced. Thus, the presence of the complex is inversely proportional to the analyte concentration in the sample. Alternatively, one can assay for the presence of the remaining unbound labelled $\alpha A$ in the aqueous medium. Methods for conducting a competitive assay, including the wash step, are well known in the art, see e.g. Mochida et al., U.S. Pat. No. 4,185,084. An example of the competitive assay format is shown below in Example 13.

The above approaches can also be applied to agglutination assays. Currently, to test different analytes, especially in agglutination assay format, a specific set of reagents have to be made for each of the analytes. This not only increases the cost of manufacturing, but also makes it impossible to perform a single multi-analyte test. The present invention presents the following advantages:

1) The anti-hapten coated particle (P-$\alpha$H) is a generic reagent, which can be used in a variety of tests.
2) The assay format makes it possible to run multi-analyte tests, i.e. to perform multiple tests simultaneously with a single specimen.

Compared to the prior art agglutination immunoassays discussed in the Background of the Invention, the present invention offers the advantages of simplicity, rapidity, clarity, economy, sensitivity and specificity. The agglutination assays presented here allow for visual detection of the result and do not involve wash and separation steps. Whereas the prior art agglutination assays require particles that are sensitized to the specific analyte to be detected and do not provide for multi-analyte tests; the present invention allows for the performance of multi-analyte test with a single specimen, and the use of a generic reagent for different tests.

Figure 5:
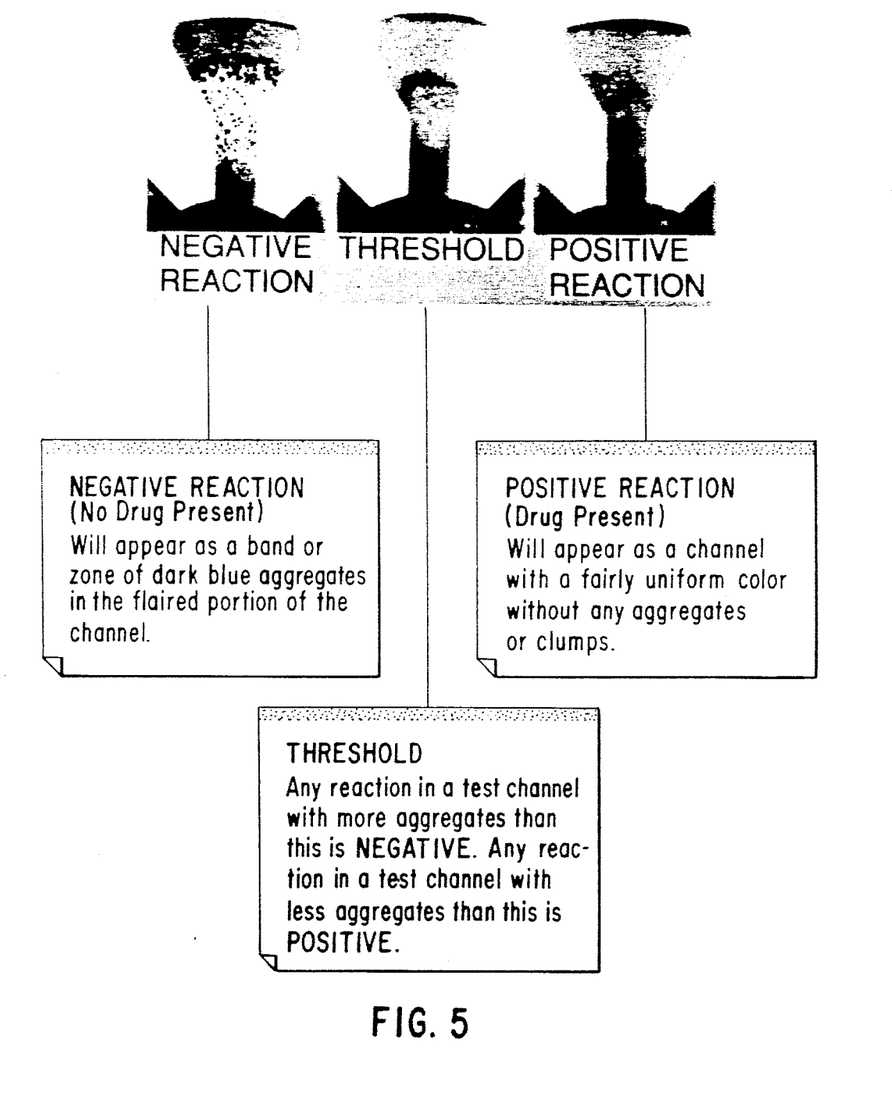
FIG. 5 presents photographs of the negative, threshold, positive reactions in drug assays.

The preferred configuration is as follows:

There are four major components in the system, the microparticle coated with an anti-hapten antibody (P-$\alpha$H), the hapten-analyte conjugate (H-A). the anti-analyte antibody ($\alpha A$) and the specimen containing the analyte (A). In the absence of the analyte (A), agglutinates of complexes of $(\alpha H)(H-A)(\alpha A)$ are formed. This results in agglutination (see FIG. 1). In the presence of the analyte (A) however, all the antibodies ($\alpha A$) are bound to the analyte (A), leaving no free antibody ($\alpha A$) to bridge the complex formation (see FIG. 2). Thus no agglutination occurs. Therefore, a negative sample results in agglutination, a positive sample gives no or reduced agglutination. FIG. 5 shows the agglutinations in the cases of: negative, threshold, and positive reactions.

One skilled in the art would also realize that the hapten-anti-hapten pairing can be replaced with ligand-receptor pairings; biotin-avidin pairings; pairings of complementary nucleic acids; and any pairing that would allow for agglutination.

MULTI-ANALYTE ASSAY

One aspect of the invention can be conducted on a multi-chamber agglutination device. Each chamber is specific for detecting a specific analyte, and contains a reagent specific for that particular analyte. The device preferably allows the sample/reaction mixture to simultaneously flow into each chamber and to react within the chamber, but does not allow the reverse flow or intermixing of the reaction mixture in one chamber with that of the other chambers.

The test for a given analyte ($A_x$) requires specific conjugate (H-$A_x$) and anti-$A_x$ antibody ($\alpha A_x$). The coated particle (P-$\alpha$H) however, is common for all analytes in this test format, and becomes a generic reagent in the system.

For multi-analyte assay, one or both of the analyte-specific components (H-$A_x$) or ($\alpha A_x$) can be pre-packaged in respective chambers for each analyte in a manifold-chamber device. The preferred devices are disclosed in U.S. patent applications Ser. No. 138,253, filed on Dec. 23, 1987, entitled "Agglutination Reaction Device" to Parsons, R. G., et al.; Ser. No. 614,762, filed Nov. 16, 1990, entitled "Improved Agglutination Reaction Device Utilizing Selectively Impregnated Material", to Forney, R. J., et al.; Ser. No. 614,895, filed Nov. 16, 1990, entitled "Improved Agglutination Reaction Device Utilizing Porous Absorbent Material" to Ropella, P. J., et al; and Ser. No. 614,817, filed Nov. 16, 1990, "Improved Agglutination Reaction Device Having Geometrically Modified Chambers", to Parsons, R. G. et al. These applications are herein incorporated by reference.

Figure 3A:
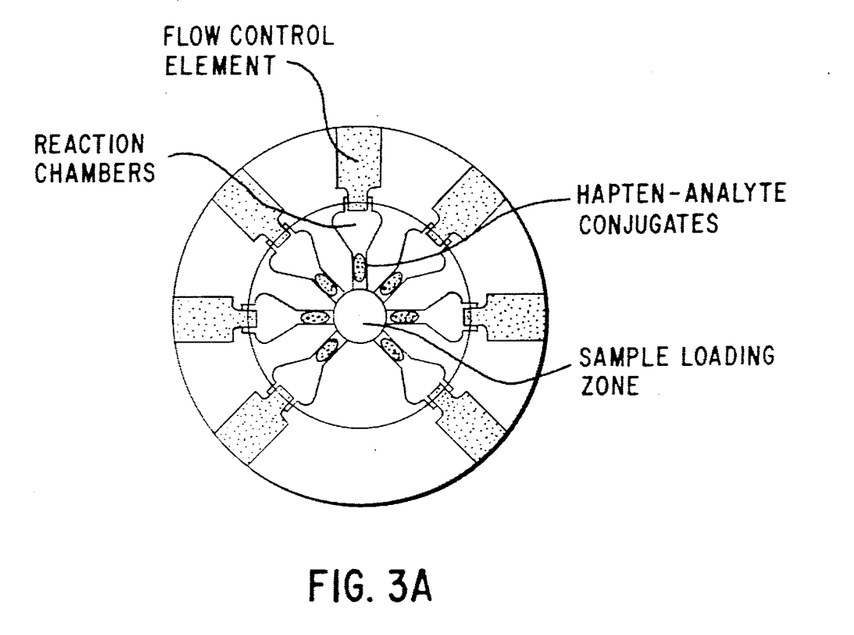
FIGS. 3A and 3B illustrate an example of a multi-analyte assay device.
Figure 3B:
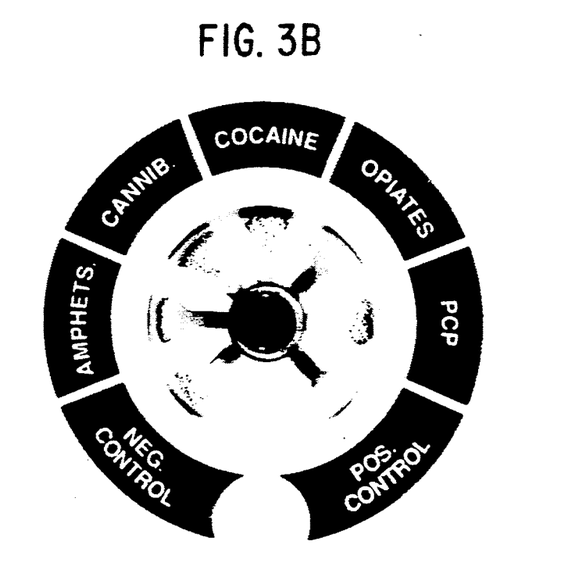

One example of these multi-chamber devices is shown in FIGS. 3A and 3B, which show two views of a multi-channel device. Preferably, different hapten-analyte conjugate (H-A) is contained within each channel. In each chamber, the conjugates (H-A) bear the specific analytes to be detected in that particular chamber. In a competitive assay, the base of the chamber can be made of the any of the solid phase materials described above. The device contains means for introducing a portion of the sample into each chamber and mixing it with the conjugates to form a mixture and yet preventing the mixture from entering another chamber. Similarly, the device would also contains means for allowing the unbound reagents to be separated from the complex of bound to the solid phase. For example, if washing is used as a separation step, the device similarly allows the wash solution to enter and exit each chamber carrying with it the unbound reagents, and yet does not allow the wash solution with the unbound reagents to enter another chamber. To achieve this latter end, the same means that separate the sample mixture in one chamber from the other may be used.

Alternatively, a simple microtiter well plate with anti-hapten antibodies bound to its wells could be used to carry out the competitive assay format, as exemplified in Example 13 below.

In the most preferred embodiment, an agglutination format is utilized for the multi-analyte assay. The H-A conjugates can be dissolved in an aqueous solution, and spotted onto the base of each of the channels and allowed to dry before the sample mixture is introduced, see e.g. Example 10 below. The mixture containing the specimen, the coated particle (P-αH) and the (αA$_x$'s) are introduced to the sample loading zone. As a portion of the mixture flows into the individual channels, the specific conjugates become mixed to form complete reaction mixtures in each channel. The agglutination reaction does not start until the reaction mixture is completed by the combination of microparticles coated with antihapten antibodies, hapten-analyte conjugate, and anti-analyte antibody. By placing different hapten-analyte conjugates (H-A$_x$, H-A$_y$, H-A$_z$...) in each channel, and using a cocktail of anti-analyte antibodies (αA$_x$, αA$_y$, αA$_z$,...) mixed with the microparticles, distinct, simultaneous assays for analytes x, y, z, etc. will occur in each respective channel. Test results for different analytes will be manifested in the individual channels which contain the specific hapten-analyte conjugates.

Alternative versions of test configurations can be realized. All versions can be implemented as the panel test format, as well as the single test format.

Examples of the components of the assays are as follows:

A. The Analytes

The analyte includes low molecular weight substances, e.g., steroids such as testosterone, progesterone, corticosterone, aldosterone; thyroid hormones such as thyroxine and triiodothyronine; physiologically active peptides e.g. bradykinin, angiotensin, thyroid hormone-releasing hormone, and luteinizing hormone-releasing hormone; physiologically active amines such as epinephrine, norepinephrine, histamine, and serotonin; prostaglandin; relatively low molecular weight substances, e.g., insulin, glucagon, adrenocorticotropic hormone, and gastrin; and high molecular weight substances, e.g., human chorionic gonadotropin, growth hormone, human placental lactogen, immunoglobulin E, alpha-fetoprotein, hepatitis B antigen. The analyte can be a hapten, an antigen, or an antibody. Examples of antigens include antigens of micro-organisms such as human immunodeficiency virus (HIV) antigens, tumor-specific antigens, cell or tissue antigens, and serum antigens. The analyte is preferably small molecules such as therapeutic drugs, drugs of abuse, and toxins.

B. The Particles and Methods for Coating Them

The particles are preferably microparticles that are visually detectable, colored microparticles which enable a direct visual readout of the presence or concentration of the analyte in the test sample without the need for using additional signal producing reagents. Materials for use as such particles include colloidal metals, such as gold and dyed particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed Jul. 9, 1987, which is incorporated by reference herein. Organic polymer latex particles can also be used. They are disclosed in co-owned and copending U.S. patent application Ser. No. 248,858, filed Sep. 23, 1988, which is incorporated by reference herein. Other particles of natural or organic polymers can also be used. Other preferred particles are cells which can agglutinate, e.g., erythrocytes, preferably fixed erythrocytes such as Duracyte ™ cells (Abbott Laboratories, North Chicago, Illinois). An example of how the erythrocytes can be fixed (i.e. stabilized) is shown in *J. Immunology*, 100 (3):641 (1988) The selection of a particular particle is not critical, so long as the particle is capable of agglutination and such agglutination can be visually detected.

Anti-hapten antibody is attached to the particle via covalent binding and/or adsorption using known methods. For example, particles such as latex particles can be passively coated with the antibodies (Hadfield, et al., *J. Imm. Methods*, supra) The method for coating antibodies onto selenium particles disclosed in the Examples below can also be used to coat other metal particles, such as gold particles. For an alternative method, see e.g. the method disclosed in Seno, U.S. Pat. No. 5,075,100 for preparing iron colloid-labeled antibodies.

C. The Haptens and Anti-Hapten Antibodies

The hapten can be any small molecule capable of eliciting immune responses in laboratory animals, usually when conjugated to a protein. Preferably, the hapten only has one antigenic site. Examples of these haptens are fluorescein, rhodamine, biotin, and dinitrophenyl groups. Anti-hapten antibodies can be produced with methods known in the art, and the antibodies can be polyclonal or monoclonal antibodies. Polyclonal antibodies can be produced for example, by injecting a host animal such as rabbit, rat, goat, mouse etc. with the hapten. Before injection, the hapten can be first conjugated with carriers such as keyhole limpet hemocyanin or bovine serum albumin. Monoclonal antibodies can be produced, e.g. according to the method disclosed in Kohler Mulstein, *Nature*, 256: 495–497 (1975). The antibodies can also be recombinant monoclonal antibodies, for example, produced according to the methods disclosed in Reading U.S. Pat. No. 4,474,893, or Cabilly et al., U.S. Pat. No. 4,816,567. Within the scope of antibodies are also antibody fragments such as Fab, F(ab')$_2$, and Fv fragments. Such fragments can be produced by known techniques.

D. The Hapten-Analyte Conjugates

The hapten-analyte conjugates, such as fluorescein-analyte conjugates are commercially available for the commonly assayed analytes, for example they are used as the tracers in Abbott Laboratories, TDX's FPIA (commercially available from Abbott Laboratories, Abbott Park, Ill.). The hapten-analyte conjugates can also be produced according to methods known in the art, such as disclosed in Wang et al U.S. Pat. No. 4,668,640.

Figure 1:
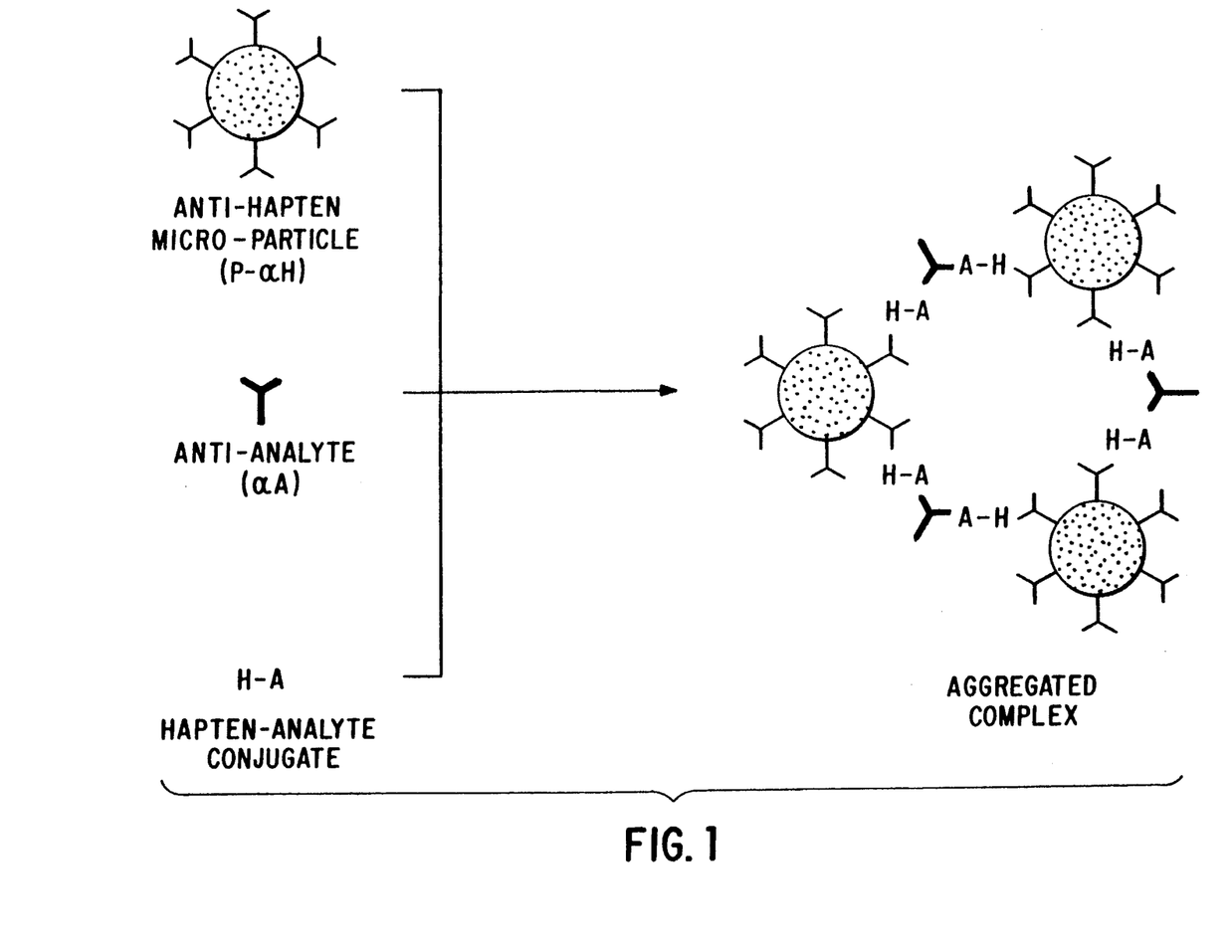
FIG. 1 illustrates the agglutination of anti-hapten microparticles in the absence of analytes.
Figure 2:
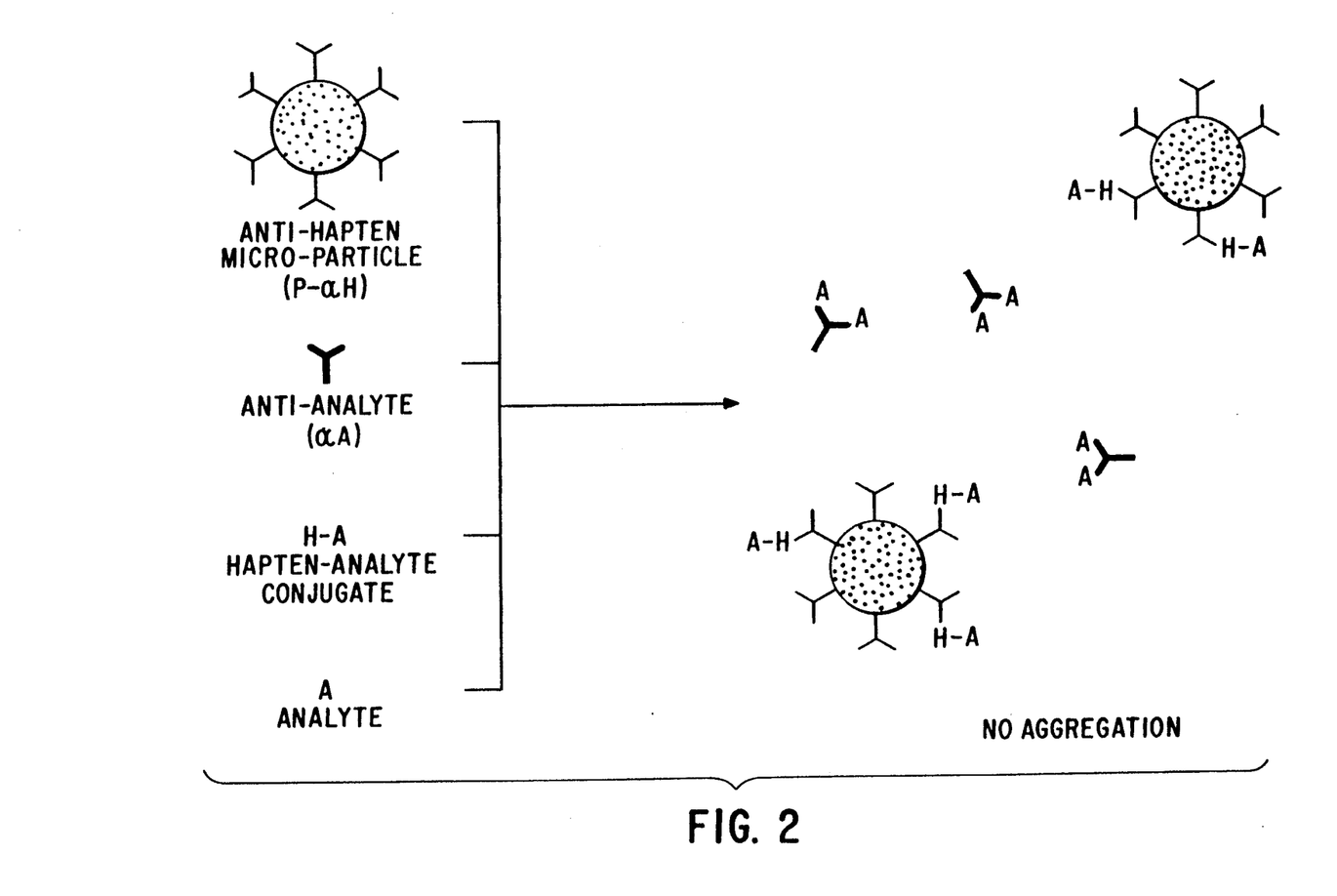
FIG. 2 illustrates the inhibition of agglutination in the presence of analytes.

The following are examples of assay formats that can be used for any analyte:

a. Competitive Assay (FIGS. 1 & 2). Members of the immunoreaction consist of the microparticle coated with anti-hapten antibody, the hapten-analyte conjugate, the anti-analyte antibody and specimen.

In the test, the analyte in the specimen competes with the hapten-analyte conjugate for the anti-analyte antibody. The more analytes are present in the specimen, the less the anti-analyte antibodies will be available for agglutination; and vice versa. Thus the observed agglutination is inversely proportional to the analyte concentration in the specimen.

b. Direct Sandwich assay for antibody.

Figure 4:
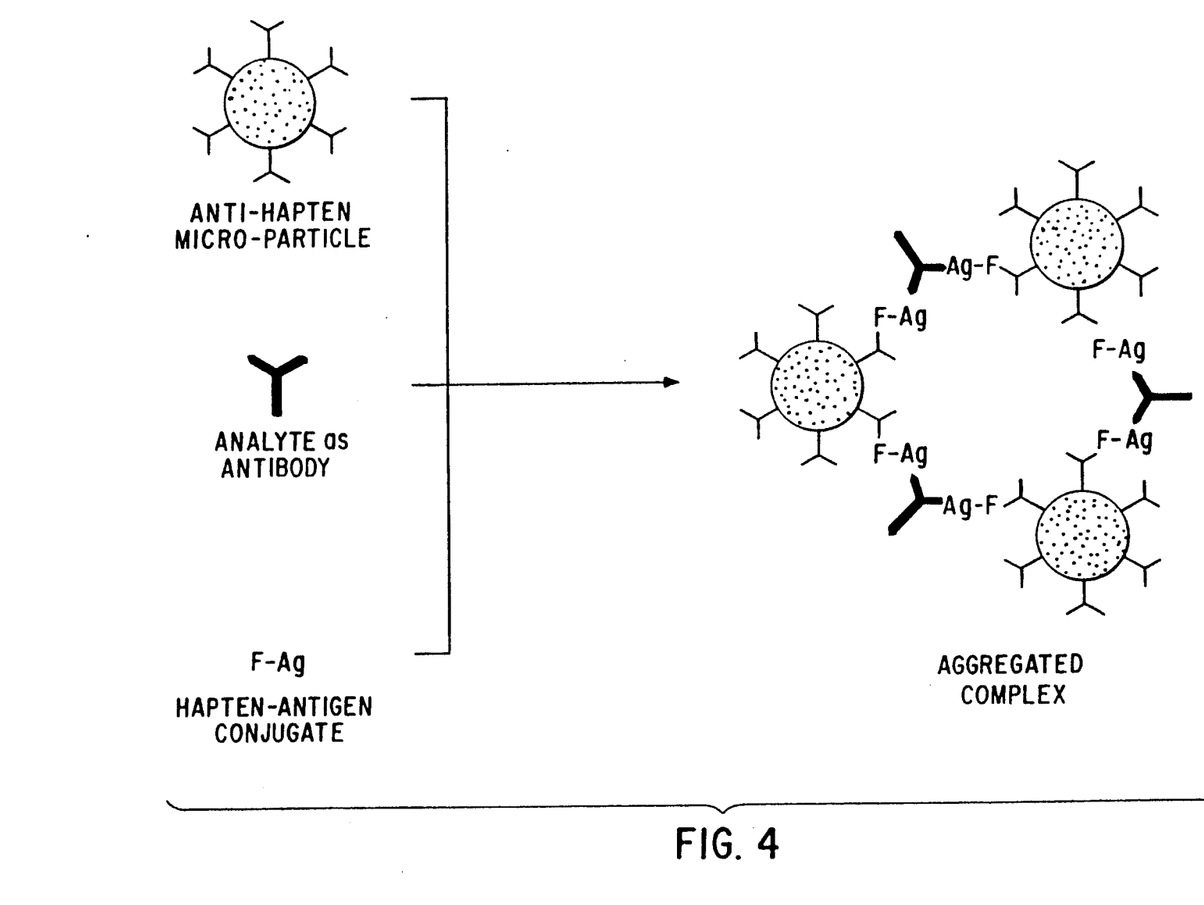
FIG. 4 illustrates a sandwich assay format for antibody test.

Similarly, the configuration can also be arranged to test for antibodies (Ab). Thus, the antibodies of interest become the analytes. The sample is mixed with the anti-hapten antibody coated microparticles (P-αH), and conjugates of the haptens with antigens for which the antibodies of interest are specific for (H-Ag). The concentration of antibodies in the sample is directly proportional to the amount of agglutination caused by the formation of complexes of (P-αH)(H-Ag)(Ab) (as shown in FIG. 4).

Dyed Particles and The Dyeing Methods

The present invention also presents dyed erythrocytes, preferably dyed fixed erythrocytes, to enhance visualization of the agglutination process. Hadfield et al., U.S. Pat. No. 4,745,075, in column 3, has suggested dyeing erythrocytes that are used agglutination assays. The patent indicated that the erythrocytes may be prepared or dyed according to standard methods, see e.g. U.S. Pat. No. 4,419,453 and German Patent Application DT-3000-483, and that particularly suitable colors include red, yellow, blue, green, black, cyan, magenta, and white.

The current invention presents erythrocytes which can be dyed, for example, red, green or blue. The dyed erythrocytes, preferably fixed erythrocytes such as the commercially available Duracyte TM cells, can be coated with antibodies and the antibodies still maintain their abilities to bind their antigens and cause agglutination of the dyed erythrocytes. Dyed particles can be used at lower concentrations than their non-dyed counterparts with comparable performance. Preferably, the dyes firmly adhere to the cells and do not leach into the surrounding assay solution. The preferred dyes for cells such as fixed erythrocytes are: Cibachrome Blue 3GA (Sigma Chemical Co., St. Louis, Mo.); the Reactive Color Series from Sigma Chemical Co., such as Reactive Red, Reactive Green, Reactive Yellow, etc.; diazonium dyes (such as Fast Black K, Fast Blue B from Sigma Chemical Co., St. Louis, Mo.); and organic dyes with Iodoacetamide or maleimide coupling chemistry (e.g. Rhodamine iodoacetamide, Rhodamine maleimide, Eosine iodoacetamide, Eosine maleimide, Tetramethylrhodamine maleimide, and Tetramethylrhodamine iodoacetamide). In the case of fixed erythrocytes, an important feature of the above listed dyes is that they couple to the erythrocytes via functional groups other than amino groups, since the erythrocytes have no or very few free amino groups available for binding dye. The most preferred dyes are those which covalently bind to the erythrocytes, preferably fixed erythrocytes. The intensities of the colors of the different particles are preferably balanced to achieve good differentiation between agglutination and lack thereof.

The dyed particles can be used in the above agglutination reactions where two or more populations of particles (of different colors) can be mixed to perform multiple assays. The different colored particles are preferably present in about equal amounts. Reactions with either of the populations of particles cause an overall change in the color of the solution which can be easily visualized. In the multi-analyte assay format using generic anti-hapten particles, other colored particles can be used, for example, differently colored latex and plastic particles. This greatly enhances one's ability to read these tests and allows for multiple tests to be run simultaneously. Thus, the invention poses an advantage over prior art where each individual assay and control are run separately, incurring extra time and labor.

EXAMPLES

Example 1

Staining of Fixed Human Erythrocytes with Coomassie Brilliant Blue R-250

Fixed human erythrocytes (Duracyte, Abbott Laboratories, supra) were suspended in 0.1M citrate buffer, pH 3.0 at a final concentration of 5% (v/v). Coomassie Brilliant Blue R-250 dye (Biorad Labs., Richmond, Calif.) was added to a final concentration of 0.5% (w/v) and the cells were allowed to incubate at room temperature for 1.5 hours. Finally the cells were alternately centrifuged (1000×G, 1 min) and washed with phosphate buffered saline (PBS, 10 mM sodium phosphate and 0.15M NaCl, pH 7.4) until the supernatant had very little residual color. The resultant suspension of cells had a dark purple color.

Example 2

Staining of Fixed Human Erythrocytes with Cibacron Blue 3GA

A 10% suspension of Duracyte TM cells was prepared in 50 mM NaOH. Cibacron Blue 3GA (Sigma Chemical Co., St. Louis, Mo.) was added to the suspension to a final concentration of 50 mg/ml. The suspension was allowed to mix at room temperature for 1.5 hours. The cells were similarly centrifuged and washed as in Example 1. The resultant cell suspension had a dark blue color.

Example 3

Staining of Fixed Human Erythrocytes with Cibacron Red 2

A 10% suspension of Duracyte TM cells was stained red using the procedure described in Example 2 and Reactive Red 2 (Sigma Chemical Co., St. Louis, Mo.). The resultant cell suspension had a red color.

Example 4

Coating of Fixed Human Erythrocytes with Anti-fluorescein

A 10% (v/v) suspension of Duracyte TM cells were coated with affinity-purified rabbit anti-fluorescein at a concentration of 100 μg/mL in the presence of 0.05% (w/v) chromic chloride in 0.1M sodium acetate buffer at pH 4.0. The suspension was incubated at 30° C. for 1 hour with occasional mixing via inverting the reaction test tube. After centrifugation (1000×G, 1 min), the cells were washed two times with 8× Volume of PBS and then incubated with 1% (w/v) human serum albumin (Sigma Chemical Co., St. Louis, Mo.) in 25 mM Tris/HCl buffer (pH 8.0) at room temperature for 30 minutes. The cells were finally resuspended in PBS (see Example 1) to a final cell concentration of 10% (v/v).

Example 5

Coating of Colloidal Selenium with Anti-fluorescein

About 57 mL of stock selenium colloid (OD550 12.3) (prepared according to the method disclosed in U.S. patent application Ser. No. 072,084, supra) was centrifuged at 750×G for 25 min. The soft pellet was suspended in 20 mL of Milli-Q water (Millipore Corp., Bedford, Mass.). The centrifugation and resuspension was repeated twice. The pH of 400 ml Milli-Q water was carefully adjusted with 0.2% sodium carbonate to 7.8. About 8.7 mL (OD 550=688) of the selenium was added to the pH 7.8 solution. Then 0.5 mg of protein-A purified rabbit-anti-fluorescein IgG was added to the selenium suspension. This was gently stirred at 2°-8° C. overnight. Bovine serum albumin (BSA, Sigma Chemical Co., St. Louis, Mo.) was added to the suspension to a concentration of 0.5%. Stirring was continued for another 2 hours. The mixture was washed as described above via centrifugation. After the last centrifugation, the pellet was suspended in 0.1% BSA, 5 mM HEPES (N-[2-hydroxyethyl]piperazine-N'-[2-ethanesulfonic acid], Sigma Chemical Co., St. Louis, Mo.), pH 7.8 to give an OD550 of 2.0 when 15 uL was diluted into 1 mL of water. This was stored at 2°-8° C.

Example 6

Coating of Colloidal Polypyrrole with Antifluorescein

Stock polypyrrole (PP) at 1 mL, ~350 OD800/ml was washed 3 times with water (1 mL) via centrifugation at 1000×G, 5 min each (International Equipment Co., Needham Height, Mass.). About 200-300 ul of the washed PP was mixed with 0.5 ml of 250 mM MES (2-[N-morpholino]ethanesulfonic acid, Sigma Chemical Co., St. Louis, Mo.) pH 7.0 and 4.5 mL water and 10-250 μg of protein-A purified rabbit anti-fluorescein IgG for 10 min. BSA was added to the mixture to a concentration of 0.05%. The suspension was mixed for another 10 min. The preparation was then washed 3 times with (1 mL) 0.5% BSA, 35 mM MES at pH 7.0. The mixture was finally suspended in 50 ul of the same buffer.

Example 7

Fixed Human Erythrocytes anti-fluorescein Assay for Cocaine Metabolites (Benzoylecognine)

One mL of anti-fluorescein-coated Duracyte TM cells (see Example 4) was resuspended in 3 ml Duracyte TM buffer (0.067M sodium phosphate at pH 8.0, 0.75M NaCl, 20 mM EDTA (ethylenediamine tetraacetic acid, Sigma Chemical Co., St. Louis, Mo.), 1.5% fetal calf serum, 6% Ampholyte (Pharmacia LKB Biotech., Piscataway, N.J.) nd 0.1% sodium azide). For this assay, 25 ul of the above anti-fluorescein Duracyte TM cells, 5 ul of sheet anti-cocaine antisera, 10 ul of the urine specimen and 5 ul of a diluted fluorescein-cocaine conjugates (TDx cocaine tracer diluted at two-fold with 0.15M NaCl; The tracer was obtained from TDx Cocaine Metabolites Kit, commercially available from Abbott Laboratories, North Chicago, Ill.) were mixed, via repeated aspirating and dispensing, and then added to a laminated test card (similar to that disclosed in Example 1 of pending U.S. application Ser. No. 07/614,817, supra, except that each card used herein contained ten reaction channels). Within 5-10 min, the viewing areas of the test cards were visually examined for agglutination patterns indicative of positive or negative results. A granular agglutination pattern in the viewing zone indicated the absence of cocaine (Benzoylecognine) in the samples (negative result). A smooth pattern without any agglutination was found when samples with Benzoylecognine were used (positive result). Twenty known benzoylecognine-positive samples and 18 samples were tested. All positive samples gave positive results and all negative samples gave negative results.

Tests for opiates, cannabinoids, amphetamine and phencyclidine were analogously configured. Known positive and negative samples for each of the analytes all give the corresponding positive and negative results respectively.

Example 8

Colloidal Selenium anti-fluorescein Assay for Phencyclidine

Phencyclidine-fluorescein conjugate (PCP tracer from TDx PCP Reagent Kit, Abbott Laboratories, supra) was mixed with a stock preparation of anti-fluorescein-coated selenium (see Example 5) at a concentration of 0.04% (%). Thirty ul of the mixture was aliquoted into each of 4 test tubes. Five ul of urine samples containing 0, 25, 60, and 120 ng/mL phencyclidine were added to each of the test tubes. Then 5 μl of anti-phencyclidine antibody (TDx PcP antisera from TDx PCP Reagent Kit, Abbott Laboratories, supra) was added. After ~8 min at room temperature, 1 ml of water was added to each of the test tubes. The mixtures were vortexed and measured for optical density at 550 nm (nanometer). The results were:

| Phencyclidine Concentration (ng/mL) | $OD_{550}$ |
| --- | --- |
| 0 | .207 |
| 25 | .515 |
| 60 | .758 |
| 120 | .823 |

Tests for opiates, cannabinoids, cocaine and Thyroxine (T4) were analogously configured except that serum instead of urine samples were used in the case of T4. The results all showed increased OD 550 with increasing concentration of analytes.

Example 9

Polypyrrole-anti-fluorescein Assay for Thyroxine

In each of 2 test tubes, 7 ul of anti-fluorescein-coated polypyrrole (see Example 6) and 2 ul of thyroxine standards containing 0 μg/mL and 0.24 μg/ml in serum, respectively, and 1.5 ul of the TDx fluorescein-thyroxine tracer and 10 ul of anti-thyroxine antisera from TDx Thyroxine Kit, Abbott Laboratories, supra, were mixed. After 10 min incubation at room temperature, the reaction mixtures were quenched with 1 ml of water. Optical density at 800 nm were measured for both mixtures. The results were:

| Thyroxine Concentration μg/ml | $OD_{800}$ |
| --- | --- |
| 0 | 1.52 |
| 0.25 | 3.73 |

Example 10

Panel Test for Abused Drugs Using Antifluorescein-coated Fixed Human Erythrocytes An aliquot (1 uL) of the TDx Fluorescein-drug tracer solution from each of the TDx assay kits for Cocaine Metabolites, Opiates, and PCP (Abbott Laboratories, supra) was placed and dried in a different channel of a laminated reaction card (The reaction card is described in Example 7). These reagent spots were positioned in the narrow, straight portions of the reaction channels. An antisera cocktail was made by mixing 20 μl from each of the three antisera solutions (Antisera solutions from $TD_x$ reagent kits) from each of the same three assay kits along with 16 μl of a 10% suspension of anti-fluorescein coated Blue Duracyte TM cells (Examples 2 and 4), and 64 μl Duracyte Buffer (Example 7). This cocktail (140 ul) was mixed with 40 ul of a normal (drug free) urine sample and 45 ul aliquots of the resultant solution were added to the laminated reaction cards and from there the solution flowed (through capillary action) into the channels having each of the three respective tracers. Within 5 minutes strong agglutination patterns were visible in each of the three channels. This experiment was repeated using samples which contained various concentrations of either Benzoylecognine, morphine, or PCP and the results are presented in the Table below:

|  | REACTION NUMBER | | | | | | | |
| --- | --- | --- | --- | --- | --- | --- | --- | --- |
|  | 1 | 2 | 3 | 4 | 5 | 6 | 7 | 8 |
| DRUG | DRUG IN SAMPLE (ng/mL) | | | | | | | |
| Benzoyl | 0 | 1670 | 0 | 0 | 1670 | 1670 | 0 | 1670 |
| Morph. | 0 | 0 | 330 | 0 | 330 | 0 | 330 | 330 |
| PCP | 0 | 0 | 0 | 167 | 0 | 167 | 167 | 167 |
| TRACER | AGGLUTINATION IN CHANNELS | | | | | | | |
| Cocaine | + | − | + | + | − | − | + | − |
| Opiate | + | + | − | + | − | + | − | − |
| PCP | + | + | + | − | + | − | − | − |

In every case when a given drug (either Benzoylecognine, Morphine, or PCP) was present in the sample, the agglutination reaction was inhibited in the reaction card channel that had the Tracer corresponding to that drug. The presence of a given drug did not have any effect on the agglutination reactions in the channels that contained tracers for the other drugs.

Example 11

Coating of Fixed Human Erythrocytes with Hepatitis B Surface Antigen (HBsAg)

Cibacron Blue 3GA-stained fixed human erythrocytes (see Example 2) were coated with monoclonal anti-HBsAg at a final concentration of 120 μg/ml using the procedure described in Example 4. The coated cells were suspended in Duracyte buffer (Example 7) at a final concentration of 10% (v/v). These cells (25 uL) were mixed with 25 ul of either serum containing 12 ng/ml HBsAg or serum without any HBsAg (25 uL) and added to the channels of laminated reaction cards (Example 7) The cells mixed with serum containing HBsAg formed strong agglutinates whereas the cells mixed with serum without H(sAg did not agglutinate.

EXAMPLE 12

Specific Color-coded Assay for HBsAg

An equal volume of the red stained (uncoated) Duracyte TM cells (Example 3) were mixed with the blue stained (anti-HBsAg coated) Duracyte TM cells (Example 11). The resulting suspension was a dark gray or black color. This mixed Duracyte TM cell suspension was mixed with serum samples containing either 25 ng/ml or zero HBsAg as described in Example 11. In the sample containing HBsAg, the blue Duracytes TM cells agglutinated and were clearly visible against a pink background (unagglutinated red Duracyte TM cells). In the sample without HBsAg, the gray-colored suspension remained as uniform color and did not show signs of agglutination.

EXAMPLE 13

Affinity purified anti-fluorescein is diluted with buffer (10 mM Tris-HCl, pH 9.0, 150 mM NaCl) to a final concentration of 50 μg/mL. 100 μL aliquots of this material is incubated in each of the wells of a 96 well microtiter plate for 12 hr at 37° C. The non-bound anti-fluorescein is next aspirated from the wells, and the wells are washed five times with 100 μL amounts of PBS containing 0.1% BSA. At this point the microtiter plate wells contain an adsorbed, non-soluble coating of anti-fluorescein (coated microtiter plate).

Mixtures (100 μL) of urine samples containing known amounts of Phencyclidine (PCP), a PCP-fluorescein conjugate, and an alkaline phosphatase labeled anti-PCP antibody, are added to the wells, such that the first well contains no free PCP, the second well contains 25 ng/mL PCP and the third well contains 250 ng/mL of PCP. The microtiter plate is incubated for 1 hour at 37° C., and the contents of each well are aspirated and the wells are washed five times with 100 μL of BS containing 0.1% BSA. Alkaline phosphatase substrate reagent (Sigma 104 Phosphatase Substrate, Sigma Chemical Co., St. Louis, Mo.) is added in 100 μL amounts to each of the wells, and after 10 minutes incubation, a yellow color is observed to be developing in the well which did not contain PCP, whereas the wells with increasing concentrations of PCP have decreasing amounts of color. In this assay, the amount of color developed is inversely proportional to the amount of PCP in the sample.

Analogous assays for other drugs (opiates, amphetamine, etc.) are performed in other wells of the same coated microtiter plate by adding samples containing mixtures of specific fluorescein conjugates of those drugs and their respective enzyme-labeled antibody pairs, in the place of the PCP-fluorescein and the enzyme-labeled anti-PCP used in the example above.

EXAMPLE 14

Aliquots (1.5 uL) of fluorescein-drug tracer solutions for amphetamines, cannabinoids cocaine, opiates, and PCP (from the respective $TD_x$ assay kits available from Abbott Laboratories, supra) are placed and dried in channels 2-6 of the laminated reaction card (FIGS. 3A and 3B show two views of the card). For a negative control, another 1.5 μL of Fluorescein labeled BSA (Sigma Chemicals, St. Louis, Mo.) diluted to 0.5 mg/mL in PBS is added to channel 1 of each card. For a positive control, channel 7 of each of the card is left without any dried reagents. An antisera cocktail with anti-fluorescein coated Duracyte TM cells is prepared as described in Example 10, however, additional antisera directed against cannabinoids and amphetamines are also added. A 200 ul sample of this antibody cocktail is mixed with 20 uL of normal (drug-free) human urine, and then introduced into the center of the reaction card. The liquid simultaneously flows into each of the channels and mixes with the reagents dried therein After 5 minutes, the appearance of aggregated cells is clearly visible in Channels 1-6. Channel 1 represents a negative reaction reference and it will show a reaction analagous to the negative assays, independent of whether negative or positive samples are run. Channels 2-6 provide the individual reactions for each of the 5 drugs (amphetamines, cannabinoids, cocaine, opiates, and PCP) corresponding to the individual drug tracers placed in the channels. The Duracyte TM cells in channel 7 do not aggregate, since no tracer or other reagents are present in this channel, and therefore it provides a positive reaction reference.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

We claim:

1. An agglutination assay method for detecting or quantifying an analyte (A) in a sample, comprising the steps of:
    (a) mixing the sample with an anti-analyte antibody, hapten-analyte conjugate and particles coated with anti-hapten antibody, and incubating for a sufficient time to allow agglutination; and
    (b) detecting or measuring the presence or absence of agglutination, wherein the amount of agglutination is inversely proportional to the amount of analyte in the sample.

2. The agglutination assay method of claim 1, wherein
    step (a) further comprises mixing the sample with uncoated particles, wherein the color of the uncoated particles is different from that of the coated particles; and
    step (b) further comprises detecting the presence of agglutination by the color of the agglutinated coated particles against the background color of the uncoated particles, and detecting the absence of agglutination by the combined colors of the coated and uncoated particles.

3. The agglutination assay method of claim 2, wherein about equal numbers of the coated and uncoated particles are used.

4. The agglutination assay method of claim 1, wherein the particles are microparticles.

5. The agglutination assay method of claim 1, wherein the particles are selected from the group consisting of cells, latex microparticles, plastic microparticles, selenium microparticles, iron microparticles, and gold microparticles.

6. The agglutination assay method of claim 5, wherein the cells are dyed erythrocytes.

7. The agglutination assay method of claim 1, wherein the analyte is a low molecular weight substance.

8. The agglutination assay method of claim 1, wherein the analyte is a high molecular weight substance.

9. The agglutination assay method of claim 1, wherein the analyte is selected from the group consisting of antigens, antibodies, and haptens, wherein said haptens are not the same as those in the hapten-analyte conjugate or those which are specifically bound by the anti-hapten antibodies coated onto the particles.

10. The agglutination assay method of claim 1, wherein the analyte is selected from the group consisting of drugs, toxins, vitamins, hormones, and enzymes.

11. The agglutination assay method of claim 10, wherein the drug is a drug of abuse or a therapeutic drug and is selected from the group consisting of phencyclidines, opiates, cannabinoids, amphetamines, cocaines, and steroids.

12. A direct agglutination assay for detecting and assaying for the presence and amount of antibody in a sample, which specifically binds to an antigen, comprising the steps of:
    (a) mixing the sample with hapten-antigen conjugate and particles coated with anti-hapten antibody, and incubating for a sufficient time to allow agglutination; and
    (b) detecting and assaying the agglutination, wherein the amount of agglutination is directly proportional to the amount of antibody in the sample.

13. An agglutination assay method for simultaneously detecting or quantifying more than one analyte in a sample, comprising the steps of:
    (a) employing a device which contains more than one chamber, wherein each chamber contains a conjugate of a hapten and an analyte to be detected;
    (b) mixing the sample with more than one antibody, each of which specifically binds to an analyte to be detected, and particles coated with anti-hapten antibodies, to form a mixture;
    (c) introducing a portion of the mixture into each chamber, whereby the portion, once introduced into the chamber would not escape and enter other chambers, and the portion becomes mixed with the conjugate in that chamber;
    (d) detecting or measuring the present of agglutination in each chamber, the amount of agglutination in each chamber being inversely proportional to the amount of analyte in the sample which is specifically being detected or measured in that chamber.

14. An agglutination assay method for simultaneously detecting more than one analyte in a sample, comprising the steps of:
    (a) employing a device which contains more than one chamber, wherein each chamber contains a conjugate of a hapten and an analyte to be detected;
    (b) mixing the sample with more than one antibody, each of which specifically binds to an analyte to be detected, and particles coated with anti-hapten antibodies, to form a mixture;
    (c) introducing a portion of the mixture into each chamber, whereby the portion, once introduced into the chamber would not escape and enter other chambers, and the portion becomes mixed with the conjugate in that chamber;
    (d) detecting by human eyes the presence of agglutination in each chamber, the amount of agglutination in each chamber being inversely proportional to the amount of analyte in the sample which is specifically being detected in that chamber.

15. The agglutination assay method of claim 14, whereby said device contains means for distributing a portion of the mixture into each chamber.

16. An agglutination assay method for simultaneously detecting or quantifying more than one analyte in a sample, comprising the steps of:

(a) employing a device which contains more than one chamber, wherein each chamber contains a conjugate of a hapten and an analyte to be detected;
(b) mixing the sample with more than one antibody, each of which specifically binds to an analyte to be detected, and particles coated with anti-hapten antibodies, to form a mixture;
(c) introducing the mixture into said device, said device containing means for distributing a portion of the mixture into each chamber, whereby the portion, once introduced into the chamber would not escape and enter other chambers, and the portion becomes mixed with the conjugate in that chamber;
(d) detecting or measuring the presence of agglutination in each chamber, the amount of agglutination in each chamber being inversely proportional to the amount of analyte in the sample which is specifically being detected or measured in that chamber.

* * * * *

UNITED STATES PATENT AND TRADEMARK OFFICE
CERTIFICATE OF CORRECTION

PATENT NO. : 5,270,166
DATED : December 14, 1993
INVENTOR(S) : Parsons, et. Al.

It is certified that error appears in the above-indentified patent and that said Letters Patent is hereby corrected as shown below:

Column 16, line 38, change "present" to --presence--.

Signed and Sealed this

Sixth Day of May, 1997

Attest:

BRUCE LEHMAN

Attesting Officer

Commissioner of Patents and Trademarks